(12) United States Patent
Boyle et al.

(10) Patent No.: US 10,548,608 B2
(45) Date of Patent: Feb. 4, 2020

(54) SOLVENT DEPRESSION OF TRANSITION TEMPERATURE TO SELECTIVELY STIMULATE ACTUATION OF SHAPE MEMORY POLYMER FOAMS

(71) Applicants: Lawrence Livermore National Security, LLC, Livermore, CA (US); The Texas A&M University System, College Station, TX (US)

(72) Inventors: Anthony J. Boyle, College Station, TX (US); Keith Hearon, Augusta, GA (US); Duncan J. Maitland, College Station, TX (US); Landon D. Nash, College Station, TX (US); Thomas S. Wilson, San Leandro, CA (US)

(73) Assignee: Lawrenece Livermore National Security, LLC, Livermore, CA (US)

( * ) Notice: Subject to any disclaimer, the term of this patent is extended or adjusted under 35 U.S.C. 154(b) by 52 days.

(21) Appl. No.: 15/579,217

(22) PCT Filed: Jun. 7, 2016

(86) PCT No.: PCT/US2016/036245
§ 371 (c)(1),
(2) Date: Dec. 4, 2017

(87) PCT Pub. No.: WO2016/200829
PCT Pub. Date: Dec. 15, 2016

(65) Prior Publication Data
US 2018/0177508 A1    Jun. 28, 2018

Related U.S. Application Data

(60) Provisional application No. 62/172,562, filed on Jun. 8, 2015.

(51) Int. Cl.
*A61B 17/12* (2006.01)
*A61L 31/06* (2006.01)
(Continued)

(52) U.S. Cl.
CPC .. *A61B 17/12181* (2013.01); *A61B 17/12031* (2013.01); *A61B 17/12113* (2013.01);
(Continued)

(58) Field of Classification Search
CPC .. A61L 31/06; A61L 2400/16; A61L 2430/36; A61L 31/14; A61L 31/146;
(Continued)

(56) References Cited

U.S. PATENT DOCUMENTS

2008/0009831 A1   1/2008 Griffin
2008/0182028 A1*  7/2008 Iu .................... C09D 11/30
                                                      427/466
(Continued)

OTHER PUBLICATIONS

The International Searching Authority, "Written Opinion of the ISA and International Search Report," dated Oct. 12, 2016 in International Application No. PCT/US2016/036245, 10 pages.
(Continued)

*Primary Examiner* — Frances Tischler
(74) *Attorney, Agent, or Firm* — Trop, Pruner & Hue, P.C.

(57) ABSTRACT

An embodiment of the invention is a shape memory polymer (SMP) foam designed to recover its original shape through exposure to a solvent. Thermo-responsive SMPs are polymers designed to maintain a programmed secondary shape until heated above their transition temperature, upon which the polymer recovers its original, or primary, shape. The thermo-responsive SMP foam is programmed to its secondary shape prior to use, typically compression of the foam to a small volume, and remains in this programmed shape until (Continued)

exposed to a selected solvent such as dimethyl sulfoxide or ethyl alcohol. Upon exposure to the solvent, the transition temperature of the SMP foam decreases below the temperature of the environment and the SMP foam actuates to its primary shape. The SMP foam is tailored to actuate upon exposure to specific solvents while minimizing or preventing actuation when exposed to water or other solvents. This selective solvent actuation can be used to increase working time of a SMP foam device, that is, the time allowed for use of a device without undesired actuation, while maintaining functional SMP actuation. Solvent actuated SMP foams can be used in various applications including, but not limited to, treatment of aneurysms and arterio-venous malformations, tissue engineering, and wound healing.

20 Claims, 4 Drawing Sheets

(51) Int. Cl.
  *A61L 31/14* (2006.01)
  *A61B 17/00* (2006.01)
(52) U.S. Cl.
  CPC .............. *A61L 31/06* (2013.01); *A61L 31/14* (2013.01); *A61L 31/146* (2013.01); *A61B 2017/00871* (2013.01); *A61B 2017/00938* (2013.01); *A61B 2017/00964* (2013.01); *A61L 2400/16* (2013.01); *A61L 2430/36* (2013.01)
(58) Field of Classification Search
  CPC .............. C08L 75/04; A61B 17/12031; A61B 17/12113; A61B 17/12181; A61B 17/1219; A61B 2017/00871; A61B 2017/00938; A61B 2017/00964
  See application file for complete search history.

(56) References Cited

U.S. PATENT DOCUMENTS

| | | | |
|---|---|---|---|
| 2011/0252781 | A1 | 10/2011 | Johnson et al. |
| 2013/0126170 | A1 | 5/2013 | Johnson et al. |
| 2013/0161026 | A1 | 6/2013 | Garza et al. |
| 2013/0211517 | A1* | 8/2013 | You .................... G02B 27/0006 623/6.62 |
| 2014/0020910 | A1 | 1/2014 | Falkner et al. |

OTHER PUBLICATIONS

Boyle, et al., "Dimethyl Sulfoxide Stimulated Actuation of Shape Memory Polymer Foam," presented Jun. 9, 2014, Biomedical Device Laboratory, Texas A&M University, College Station, TX, USA.
Boyle, et al, "Solvent stimulated actuation of polyurethane-based shape memory polymer foams using dimethyl sulfoxide and ethanol," May 24, 2016, Smart Materials and Structures, vol. 25, No. 7, IOP Publishing Ltd.
Rodriguez, et al., "Reticulation of low density shape memory polymer foam with an in vivo demonstration of vascular occlusion," Aug. 11, 2014, pp. 102-114, Journal of the Mechanical Behavior of Biomedical Materials, Elsevier Ltd.
Sampei, et al., "Histological changes in brain tissue and vasculature after intracarotid infusion of organic solvents in rats," Neuroradiology, 1996, pp. 291-294, vol. 38, Springer-Verlag.
Mottu, et al., "Organic Solvents for Pharmaceutical Parentals and Embolic Liquids: A Review of Toxicity Data," PDA Journal of Pharmceutical Science & Technology, Nov./Dec. 2000, pp. 456-469, vol. 54, No. 6.
Hamada, et al., "A nonadhesive liquid embolic agent composed of ethylene vinyl alcohol copolymer and ethanol mixture for the treatment of cerebral arteriovenous malformations: experimental study," Journal of Neurosurgery, Oct. 2002, pp. 889-895, vol. 97.
Yang, et al., "Effects of moisture on the thermomechanical properties of a polyurethane shape memory polymer," Polymer, 2006, pp. 1348-1356, vol. 47, Elsevier Ltd.
LV, et al., "Shape-Memory Polymer in Response to Solution," Advanced Engineering Materials, 2008, pp. 592-595, vol. 10, No. 6, Wiley-VCH Verlog Gmbh & Co. KGoA, Weinheim.
Du, et al., "Solvent induced shape recovery of shape memory polymer based on chemically cross-linked poly(vinyl alcohol)," The Royal Society of Chemistry, 2010, pp. 3370-3376, vol. 6, www.rsc.org/softmatter.
Haibao Lu, "A Simulation Method to Analyze Chemo-Mechanical Behavior of Swelling-Induced Shape-Memory Polymer in Response to Solvent," Journal of Applied Polymer Science, 2011, pp. 1137-1146, vol. 123, Wiley Periodicals, Inc.
Lu, et al., "A phenomenological thermodynamic model for the chemo-responsive shape memory effect in polymers based on Flory-Huggins solution theory," Polymer Chemistry, 2014, pp. 1155-1162, vol. 5, The Royal Society of Chemistry.
Lu, et al., "Quantiative separation of the influence of hydrogen bonding of ethanol/water mixture on the shape recovery behavior of polyurethane shape memory polymer," Smart Materials and Structures, 2014, pp. 1-8, vol. 23, IOP Publishing, Ltd., United Kingdom.
Wilson, et al., "Shape Memory Polymers Based on Uniform Aliphatic Urethane Networks," Journal of Applied Polymer Science, 2007, pp. 540-551, vol. 106, Wiley Periodicals, Inc.
Yu, et al., "The effect of moisture absorption on the physical properties of polyurethane shape memory polymer foams," Smart Materials and Structures, 2011, pp. 1-6, vol. 20, IOP Publishing Ltd, USA.
Singhal, et al., "Ultra Low Density and Highly Crosslinked Biocompatible Shape Memory Polyurethane Foams," Journal of Polymer Science Part B: Polymer Physics, 2012, pp. 724-737, vol. 50, Wiley Periodicals, Inc.
Singhal, et al., "Controlling the Actuation Rate of Low-Density Shape-Memory Polymer Foams in Water," Macromolecular Chemistry and Physics, Macromolecular Journals, 2013, pp. 1204-1214, vol. 214, Wiley-VCH Verlag GmbH & Co., KGaA, Weinheim.
Hasan, et al., "Effects of Isophorone Diisocyanate on the Thermal and Mechanical Properties of Shape-Memory Polyurethan Foams," Macromolecular Chemistry and Physics, Macromolecular Journals, 2014, pp. 2420-2429, vol. 215, Wiley-VCH Verlag GmbH & Co., KGaA, Weinheim.
The International Searching Authority, "International Preliminary Report on Patentability," dated Dec. 12, 2017 in International Application No. PCT/US2016/036245, 8 pages.

* cited by examiner

SOLVENT DEPRESSION OF TRANSITION TEMPERATURE TO SELECTIVELY STIMULATE ACTUATION OF SHAPE MEMORY POLYMER FOAMS

PRIORITY CLAIM

This application claims priority to U.S. Provisional Patent Application No. 62/172,562 filed on Jun. 8, 2015 and entitled "Solvent Depression of Transition Temperature of Selectively Stimulate Actuation of Shape Memory Polymer Foams", the content of which is hereby incorporated by reference.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

TECHNICAL FIELD

Embodiments of the invention are in the field of shape memory polymers.

BACKGROUND

Thermally actuated shape memory polymers (SMPs) are a special class of materials that are capable of switching between a primary and a secondary shape upon a heat stimulus. These versatile materials are used for a wide range of applications such as biomaterials, textiles, and automotive. Previously synthesized SMP foams have proven to rapidly occlude aortic aneurysms and the resulting clot is stable up to 90 days. These SMP foams can further be utilized for a neurovascular occlusion device due to their ultra-low density, which allows for the material to be crimped to a small geometry and delivered to the aneurysm via catheter.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Figure 1:
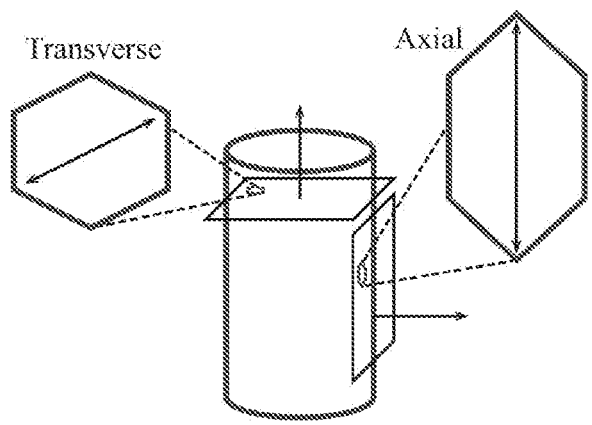
FIG. 1 includes a transverse anisotropy of SMP foams. Pores are shown with diameter measurements in the transverse and axial direction, where the axial direction is parallel with the direction of foaming.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner "Connected" may indicate elements are in direct physical or electrical contact with each other and "coupled" may indicate elements co-operate or interact with each other, but they may or may not be in direct physical contact.

An embodiment of the invention is a SMP foam designed to recover its original shape through exposure to a solvent. Thermo-responsive SMPs are polymers designed to maintain a programmed secondary shape until heated above their transition temperature, upon which the polymer recovers its original, or primary, shape. The thermo-responsive SMP foam is programmed to its secondary shape prior to use, typically compression of the foam to a small volume, and remains in this programmed shape until exposed to a selected solvent such as dimethyl sulfoxide or ethyl alcohol. Upon exposure to the solvent, the transition temperature of the SMP foam decreases below the temperature of the environment and the SMP foam actuates to its primary shape. The SMP foam is tailored to actuate upon exposure to specific solvents while minimizing or preventing actuation when exposed to water, an aqueous physiologic environment, or other solvents. This selective solvent actuation can be used to increase working time of a SMP foam device, that is, the time allowed for use of a device without undesired actuation, while maintaining functional SMP actuation. Solvent actuated SMP foams can be used in various applications including, but not limited to, treatment of vascular defects such as aneurysms and arterio-venous malformations, tissue engineering, and wound healing.

Utility

Solvent actuated SMP foams can be implemented in various products, particularly medical devices for endovascular embolization treatments and other applications, to take advantage of rapid, controlled actuation and selective solvent exposure.

Significance

SMP foams have been proposed to be advantageous for several applications in various industries with differing application environments and limitations. SMP foams have shown promise in biomedical applications, especially for embolization treatments. Solvent actuation of SMP foams is advantageous for temperature sensitive applications as well as in applications or environments where heat cannot be delivered to the SMP foam effectively. This includes biomedical applications where even minimal heating of the environment can cause tissue damage and necrosis or possibly result in device failure. Solvent actuation enables rapid, controlled SMP shape recovery without requiring external energy sources to heat the polymer above its glass transition temperature. Furthermore, the SMP foams can be tailored to selectively respond to specific solvents with minimal or no recovery when exposed to water or other solvents. This is advantageous in applications and environments where the device must maintain its programmed secondary shape during exposure to solvents. For example, SMP foams for endovascular applications are exposed to water, saline, or blood during the procedure, during which undesired device actuation can lead to device or treatment failure. Solvent actuation enables use of SMP foams tailored to prevent actuation with water exposure while maintaining the ability to control the device actuation throughout the entire procedure.

Advantages

Advantages of an embodiment are the physical morphology and chemical composition of the SMP foam that result in unique physical properties as well as rapid, controlled, and selective solvent actuation. The proposed solvent actuated SMP foams exhibit a porous geometry with low densities, strong mechanical properties, and excellent shape memory capacity. These properties lead to high volume to surface area ratios and high volume expansion values that are advantageous for several applications, including vascular occlusion. Solvent induced actuation by depression of glass transition temperature has been reported in the literature for non-foamed styrene-based SMPs with dimethylformamide and non-foamed poly(vinyl alcohol)-based SMPs with water, methanol, dimethylformamide, acetic acid, and ethylene glycol. Solvent actuation of non-foamed polyurethane SMPs has been reported in the literature using water and ethanol. However, only water has been reported in the literature as a solvent for actuation of polyurethane SMP foams. Using water as the activating solvent can enable time delayed passive expansion for medical devices in an aqueous environment at body temperature by controlling moisture diffusion rates, but does not enable on-demand expansion using an external stimulus. The proposed SMP foams allow for full actuation control in aqueous environments, i.e. no actuation during long exposure times to water while maintaining the ability to stimulate actuation with a secondary solvent.

An embodiment includes a hydrophobic SMP foam composition for preferential actuation when exposed to perflourocarbon solvents or perflourocarbon emulsions. The polymer is engineered to facilitate rapid perflourocarbon diffusion, while limiting moisture uptake. To achieve this, alcohol components in the urethane synthesis would include perfluoronated diols. The alcohol components in the urethane synthesis may include fluorinated diols such as 1H,1H,4H,4H-Perfluoro-1,4-butanediol, 1H,1H,5H,5H-Perfluoro-1,5-pentanediol, Fluorinated diethylene glycol monomethyl ether, 1H,1H,6H,6H-Perfluoro-1,6-hexanediol, Fluorinated triethylene glycol, 1H,1H,8H,8H-Perfluoro-1,8-octanediol, Fluorinated tetraethylene glycol, 1H,1H,9H,9H-Perfluoro-1,9-nonanediol, 1H,1H,10H,10H-Perfluoro-1,10-decanediol, 1H,1H,12H,12H-Perfluoro-1,12-dodecanediol. These diols would shift the solubility parameters of the polymer to facilitate better perflourocarbon diffusion. Another embodiment includes supercritical gas blowing of a hydrophobic post polymerization crosslinkable SMPs. For instance, a hydrophobic, aliphatic thermoplastic with regularly spaced alkene groups in the backbone is extruded into a foam by infusing the extrusion melt with supercritical nitrogen or carbon dioxide. Alternatively, the gas infused polymer melt can be injected into a mold to form a porous injection molded part. Once formed, the foam is irradiated with electron beam radiation to crosslink the alkene segments and impart shape memory capacity. This hydrophobic, crosslinked SMP foam could be compressed to facilitate catheter delivery into the body, and remain compressed under aqueous physiologic conditions. However, this material can be plasticized with injected lipid emulsion, perfluorocarbons, or other biocompatible hydrophobic solvents or oils to lower the transition temperature below body temperature to facilitate body temperature expansion.

Enablement

In an embodiment a SMP foam is synthesized and fabricated using diisocyanate monomers (e.g., hexamethylene diisocyanate, trimethylhexamethylene diisocyanate, and isophorone diisocyanate), polyfunctional diols (e.g., hydroxypropyl ethylenediamine and triethanolamine) with surfactants, catalysts, and blowing agents. Varying diisocyanate monomers and their ratios within the polymer can be used to tailor the foam for actuation using specific solvents. The components are combined and cured in an oven. After polymerization and foaming, the foam is post processed for cleaning and fabrication into its primary shape.

Next, the SMP foam described immediately above is programmed to its secondary shape by uniformly heating the foam above its glass transition temperature and straining the polymer to the secondary shape while heated. The SMP foam is then cooled below its transition temperature while constrained in the secondary shape. For a given application, the SMP foam is delivered to the desired location for actuation, during which it maintains its programmed shape.

Next, the selected solvent is delivered to the SMP foam, upon which the transition temperature of the foam is decreased below the environment temperature and the SMP foam actuates to its primary shape. After SMP foam actuation, the solvent is then flushed or otherwise removed. Solvents can include, but are not limited to, isopropyl alcohol, acetic acid, dimethyl sulfoxide, cumene, ethyl acetate, formic acid, lactic acid, ethyl alcohol, or perfluorocarbons such as perflourodecalin, perflourophenanthrene, or perflouro-n-hexane, depending on the application requirements. For example, ethanol would not be a good solvent candidate for neurovascular device deployment due to ethanol sensitivity of the surrounding tissue. However, ethanol could still be used to deploy devices in peripheral vessels. Neurovascular applications would be better suited for perflourocarbon emulsions, other solvents, or oils that are more compatible with brain tissue.

An example application of a solvent actuated SMP device is an embolic foam for endovascular vessel occlusion. For this application, SMP foam is compressed to a small volume and delivered through catheter to the disease site. During delivery, the SMP foam maintains its compressed secondary shape while exposed to water, saline, and blood.

Once at the disease site, a selected solvent is injected through the catheter to stimulate actuation of the SMP foam to its primary expanded shape in order to fill a volume.

SMP foam chemical and physical properties should be tailored to a specific application's requirements and for the selected solvent. This may require additional studies to characterize the SMP foam mechanical and actuation properties for the application and selected solvent.

Additional Discussion

Solvent exposure has been investigated as an alternative SMP actuation trigger to direct heating or stimulation by electricity, light, or magnetic fields. Solvent stimulated actuation avoids limitations of direct heating actuation in endovascular applications including poor energy delivery to devices due to blood flow heat convection and risk of heat induced tissue damage. However, previous studies have focused on water as the actuating solvent, which is disadvantageous for endovascular applications as devices are exposed to water throughout the entire procedure. Polyurethane SMP foams have been reported as water-responsive materials, exhibiting depressed Tg when exposed to water which actuates and expands compressed devices in physiological conditions. For water-responsive embolic devices such as the hydrogel-coated platinum coils and SMP foam implants, endovascular delivery and device repositioning can be significantly impeded or halted due to device swelling or expansion. Singhal et al. reported that increasing hydrophobicity of polyurethane SMP foams resulted in delayed moisture plasticized self-actuation. Although water stimulated actuation design of SMPs provides simpler clinical procedures and reduced risk of tissue damage due to a heating device for actuation, the procedure is dependent on inconsistent actuation timing.

Sufficient working time, the time the device can be repositioned and retracted back into the microcatheter prior to self-actuation, through SMP foam hydrophobicity has yet to be achieved without severely extending the time for self-actuation or completely preventing it at physiological conditions. Solvent actuation of SMP materials using organic solvents can provide clinician initiated and controlled actuation without direct heating. Organic solvent actuated SMP foams that exhibit significantly delayed or no self-actuation in water provide long working times for clinicians while retaining expansion capabilities for improved aneurysm filling over platinum coils.

However, the injection of organic solvents during endovascular procedures can result in pharmacological and toxicological effects on the tissues. Dimethyl sulfoxide (DMSO) has been used as a solvent in commercially available liquid embolic materials for treatment of intracranial aneurysms and arteriovenous malformations. The liquid embolic is a thermoplastic polymer dissolved in DMSO. The polymer comes out of solution when injected into the blood. This is a different chemical phenomenon than a solvent soaking into our SMP foam to depress Tg. Embodiments of foams described herein are not able to dissolve in any solvent because they are thermoset. Liquid embolic treatments implement a polymer dissolved in DMSO at 92-94% by volume that is carefully injected and subsequently allowed to precipitate out of the DMSO solution by blood flow. Intra-arterial infusion of anhydrous DMSO has resulted in full-thickness angionecrosis and severe vasospasm. However, low dose volumes of 0.5-0.8 mL with slow dose durations over 30-120 seconds have been shown to result in significantly less angiotoxicity. In addition, the LD50 for lysis of red blood cells as total volume percent in whole blood has been reported for DMSO as 5.1%. In comparison, the use of ethanol resulted in a LD50 for red blood cell lysis of 21.2%. Ethanol has also been previous studied for liquid embolic applications and use as a parenteral solvent with injections at concentrations ranging 10-100% depending on application. Intra-arterial infusions using ethanol at high concentrations of 70% have produced histological changes and full-thickness angionecrosis while infusions with concentrations of 10-40% resulted in necrosis of only the intimal and partially of the medial layer. Though different solvents will result in varying degrees of angiotoxicity, studies with both DMSO and ethanol indicated that decreasing the injected solvent concentration resulted in reduced toxicity. Therefore, characterizing the SMP foam expansion at varying solvent concentrations is imperative to determining the clinical feasibility of solvent actuation.

The feasibility of using organic solvent stimulated actuation of SMP foams has yet to be fully understood, either in general or for endovascular applications. This works aims to investigate if rapid SMP actuation can be achieved and at what concentration of solvent in water is necessary for clinically relevant expansion times using current hydrophobic SMP foams. Solvent stimulated actuation is a potentially useful alternative for neurovascular embolic foam device actuation in intracranial aneurysm treatment, though the method is applicable to several SMP systems for many applications, including non-biomedical. Thus, the work proposed here focuses on developing and characterizing solvent actuation of SMP foams as a foundation and for broad clinical application (and beyond including non-medical applications), not only for intracranial aneurysm treatment.

SMP foam compositions with varying hydrophobicity will be investigated for changes in mechanical properties and expansion kinematics when exposed to water and organic solvents. SMP foam compositions with hydrophobic monomers for increased working time in physiological conditions will be investigated. DMSO and ethanol solutions in water will be investigated as both solvents have been previously studied as liquid embolic solvents for intracranial use.

Thermo-mechanical testing will be conducted on the selected SMP foam compositions with and without solvent exposure. Differential scanning calorimetry (DSC) will be used to characterize the glass transition of the SMP foams where Tg will be measured at the midpoint of the transition. Each SMP foam composition will be tested using DSC for both dry and after exposure to solvent conditions. For DSC testing of solvent exposed SMP foam samples, the sample will be submerged in water or organic solvent at 37° C. for several minutes and mechanically dried to remove non-adsorbed solvent before placing in the DSC.

Expansion kinematics of SMP foams in water and organic solvents will also be characterized to measure the working time and actuation time of SMP foams. SMP foam cylindrical samples will be radially compressed over a thin wire and suspended in solvent solution held at 37° C. and images will be recorded at specific time-points. Each SMP foam composition will be tested in varying concentrations of each organic solvent with water. The images will be analyzed to measure the dimensions of the SMP foam samples as a function of time submerged in solution. From these measurements, the working time in water and actuation time, i.e. the time for complete SMP foam expansion, in solvent solutions will be determined. Working time and actuation time are used for assessing the feasibility of solvent stimulated actuation in general.

Methods

SMP Foam Fabrication

Polyurethane-based SMP foams were synthesized using a three step protocol with aliphatic isocyanate and hydroxyl monomers as previous reported. Trimethyl-1,6-hexamethylene diisocyanate, 2,2,4- and 2,4,4-mixture (TMHDI, TCI America Inc.), isophorone diisocyanate (IPDI, 98%; Sigma-Aldrich Inc.), N,N,N',N'-tetrakis(2-hydroxypropyl) ethylenediamine (HPED, 99%; Sigma-Aldrich Inc.), triethanolamine (TEA, 98%; Sigma-Aldrich Inc.), DC 198 (Air Products and Chemicals, Inc.), DC 5943 (Air Products and Chemicals, Inc.), T-131 (Air Products and Chemicals, Inc.), BL-22 (Air Products and Chemicals, Inc), Enovate 245fa Blowing Agent (Honeywell International, Inc.) and deionized (DI) water (>17 MΩ cm purity; Millipore water purifier system; Millipore Inc.) were used as received. SMP foam compositions were synthesized with 0, 10, and 20 mol % of IPDI, with the remaining mol % of isocyanate being TMHDI, as previously reported by Hasan et al. The SMP foam compositions are denoted by the respective mol % of IPDI as 0IPDI, 10IPDI, and 20IPDI.

SMP foams were processed after synthesis before being cut to test geometry. SMP foam blocks were reticulated using a mechanical wire punch apparatus as previously reported by Rodriguez et al. 8 mm diameter, 2-3 cm long cylindrical samples were cut from the foam blocks using a biopsy punch. The foam samples were radially compressed to 1 mm diameter using a SC250 stent crimper (Machine Solutions, Inc., Flagstaff, Ariz.) heated to 100° C. and then heated to expand to their original shape. SMP foam cylinders were then acid etched and cleaned under sonication and then dried under vacuum as previously reported. Foam samples were then stored in a sealed container with desiccant.

SMP Foam Density and Pore Diameter

SMP foam density was measured for each composition. Bulk foams were cut into cubes using a resistive wire cutter from three sections along the foaming axis in accordance with ASTM standard D-3574. The length of each cube edge was measured using calipers to calculate volume, mass was measured for each foam cube, and density was calculated.

Pore diameter was measured for each SMP foam composition. The foam pores are transverse isotropic about the foaming axis as shown in FIG. 1. Each pore is approximately uniform diameter in the transverse direction and elongated in the direction of foaming in the axial direction. Slices with 1 mm thickness of cleaned SMP foam cylinders were cut in the axial and transverse directions and imaged using light microscopy. ImageJ software (National Institutes of Health, Bethesda, Md.) was used to measure the maximum diameter of each pore within a 16 mm$^2$ area of foam. Diameter values of pores with an area of 0.2-2.0 mm$^2$ in the transverse direction and 0.5-3.0 mm$^2$ in the axial direction were recorded. Pore diameters of three samples were averaged for each composition for each direction.

Differential Scanning Calorimetry

Differential scanning calorimetry (DSC) was used to measure the glass transition temperature ($T_g$) of the SMP foam compositions. A Q-200 DSC (TA Instruments, Inc., New Castle, Del.) was used to acquire thermograms for 6-12 mg samples of dry SMP foams in aluminum trays. For the first cycle, the temperature was decreased to −40° C. at 10° C./min and held isothermal for 2 minutes. The temperature was then increased to 120° C. at 10° C./min and held isothermal for 2 minutes. The second cycle consisted of reducing the temperature to −40° C. at 10° C./min, holding isothermal for 2 minutes, and then raising the temperature to 120° C. at 10° C./min $T_g$ was recorded from the second cycle at the half height of the thermal transition curve using TA instruments software. $T_g$ was recorded for 3 samples per foam composition.

DSC was also used to measure the $T_g$ of the SMP foam compositions after submersion in solvent. SMP foam cylinders were submerged in water, dimethyl sulfoxide (DMSO), and ethanol (EtOH) at 37° C. for 10 minutes. Foam samples were then compressed by hand between laboratory grade chemical wipes once and compressed between laboratory grade chemical wipes to 1 metric ton for 2 minutes using a #3851-0 hydraulic press (Carver, Inc., Wabash, Ind.). A Q-200 DSC used to acquire thermograms for 6-12 mg samples of solvent saturated SMP foam. For the first cycle, the temperature was decreased to −40° C. at 10° C./min and held isothermal for 2 minutes. The temperature was then increased to a peak temperature, depending on test solvent, at 10° C./min and held isothermal for 2 minutes. The peak temperature was 80° C. for water and DMSO samples and 60° C. for EtOH samples. The second cycle consisted of reducing the temperature to −40° C. at 10° C./min, holding isothermal for 2 minutes, and then raising the temperature to the peak temperature at 10° C./min $T_g$ was recorded from the second cycle at the half height of the thermal transition curve using TA instruments software. $T_g$ was recorded for 3 samples per foam composition.

Dynamic Mechanical Analysis

Dynamic mechanical analysis (DMA) was performed to determine the mechano-thermal transitions in various solvents. A TT-DMA (Mettler-Toledo AG, Schwerzenbach, Switzerland) was used to perform both kinetic and temperature sweeps. Foam cylinders (6 mm diameter and 5 mm length) were axially heated to 100° C. and axially compressed to 0.8 mm before cooling to room temperature under compression.

Temperature sweeps were used to find the storage modulus (E') and loss modulus (E"), with the peak ratio of E'/E" (tan δ) recorded as the glass transition temperature. Solvent was cooled to 5° C. or the freezing point of the solvents before being ramped to approximately 70° C. at a rate of 1° C./min Four samples were examined for each. For kinetic experiments, solvent was heated to 50° C. Measurements were started on the material as it was submerged. E' vs time was plotted, with the time to relaxation taken as the intersection of the straight line values for the relaxed E' and decreasing E' values. Kinetic experiments were correlated with temperature sweeps to ensure measurement accuracy.

Shape Recovery in Solvent Solutions

Shape recovery was measured over time for each SMP foam composition in solvent solutions with varying concentration. SMP foam cylinders with 2.5 mm diameter and 2-3 cm length were cut from cleaned and dried samples using a biopsy punch. A 0.09 mm diameter nickel-titanium (nitinol) wire (Nitinol Devices & Components, Inc., Fremont, Calif.) was placed through the cylinder axis. The sample diameter and length were measured for each SMP foam sample using calipers. The SMP foam cylinders were radially compressed to 0.30-0.34 mm diameter using a SC250 stent crimper heated to 100° C. Compressed samples were stored in a sealed container with desiccant for minimum 24 hours before testing. Compressed samples were then imaged and the sample diameter and length were measured using ImageJ software. Precompressed was calculated for the cylinders.

SMP foam samples were submerged in solvent solutions held at 37±1° C. and imaged at fixed time intervals. An aluminum fixture was used to suspend the foam samples in the solution and act a reference scale. Samples were submerged in solution and were imaged at 1 min intervals for 10 min of submersion and then at 5 min intervals to 30 min total submersion time. ImageJ software was used to measure the actuated diameter and length of actuated sections at each time point. Actuated volume was calculated for the cylindrical samples at each time point. Volume recovery at each time point was calculated using Equation 1.

$$\text{Volume Recovery} = \left(\frac{\text{Volume}_{Actuated}}{\text{Volume}_{Precompressed}}\right) \times 100 \quad \text{Equation 1}$$

Volume recovery was measured for 3 samples of each SMP foam composition in water, DMSO, and EtOH solutions. SMP foam samples were tested in DMSO concentrations of 100, 90, 80, 40, and 0 vol % in water and in EtOH concentrations of 100, 80, 50, 20, and 0 vol % in water.

Results

SMP Foam Density and Pore Diameter

Average density and average pore diameter in both transverse and axial directions for each SMP foam composition is shown in Table 1. All SMP foams compositions exhibited transverse anisotropy where pore diameter in axial direction is greater than in the transverse direction.

TABLE 1

SMP Foam Density and Pore Diameter

| SMP Foam Composition | Density (g/cm$^3$) | Transvere Pore Diameter (μm) | Axial Pore Diameter (μm) |
|---|---|---|---|
| 0IPDI | 0.0138 ± 0.0009 | 630 ± 371 | 931 ± 431 |
| 10IPDI | 0.0111 ± 0.0003 | 468 ± 282 | 766 ± 425 |
| 20IPDI | 0.0121 ± 0.0002 | 548 ± 296 | 944 ± 408 |

Differential Scanning Calorimetry

Average $T_g$ values for each SMP foam composition in the dry condition and after submersion in water, DMSO, and EtOH are shown in Table 2. $T_g$ values were greatest in the dry condition and lowest after submersion in EtOH for all SMP foam compositions. 20IPDI was the only composition to exhibit a water submerged $T_g$ above body temperature of 37° C. Increasing IPDI content resulted in an increase in $T_g$ in all cases when measured by DMA, due to decreased bond rotation. However, 10IPDI foams demonstrated lower $T_g$ than both 0IPDI and 20IPDI foams with solvent exposure when measured by DSC. This suggests increased plasticization of 10IPDI foams, particularly in DMSO, though there is insufficient data to conclude any statistical significance. From these results, it's suggested that increasing IPDI content is effective at muting or preventing SMP actuation in water while allowing for actuation in DMSO and EtOH.

TABLE 2

Dry and Solvent Submerged SMP Foam $T_g$

| SMP Foam Composition | Density (g/cm$^3$) | Transverse Pore Diameter (μm) | Axial Pore Diameter (μm) |
|---|---|---|---|
| 0IPDI | 0.0138 ± 0.0009 | 630 ± 371 | 931 ± 431 |
| 10IPDI | 0.0111 ± 0.0003 | 468 ± 282 | 766 ± 425 |
| 20IPDI | 0.0121 ± 0.0002 | 548 ± 296 | 944 ± 408 |

Dynamic Mechanical Analysis

TABLE 3

| SMP Foam Composition | Dry $T_g$ (° C.)[citations] | Water $T_g$ (° C.) | DMSO $T_g$ (° C.) | EtOH $T_g$ (° C.) |
|---|---|---|---|---|
| 0IPDI | 81.9 ± 1.2 | 45.9 ± 1.4 | 28.3 ± 5.7 | 18.0 ± 1.1 |
| 10IPDI | 73.7 ± 1.3 | 50.8 ± 0.8 | 33.2 ± 0.6 | 18.3 ± 2.8 |
| 20IPDI | 78.7 ± 1.6 | 61.4 ± 0.6 | 41.0 ± 3.0 | 21.9 ± 8.39 |

Shape Recovery in Solvent Solutions

Figure 2:
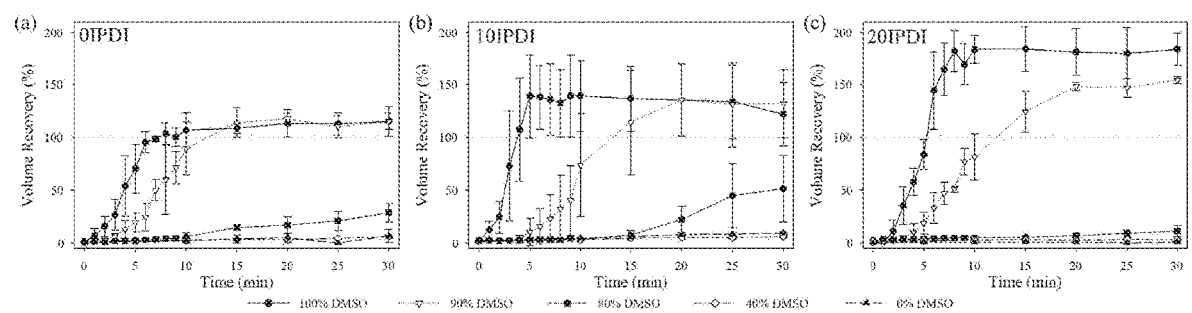
FIG. 2 depicts volume recovery in DMSO solutions. Volume recovery is shown over time submerged in DMSO solutions with varying concentrations for SMP foam compositions of (a) 0IPDI, (b) 10IPDI, and (c) 20IPDI. A dashed line is shown at 100% volume recovery to indicate where the actuated volume equals the precompressed volume.
Figure 3:
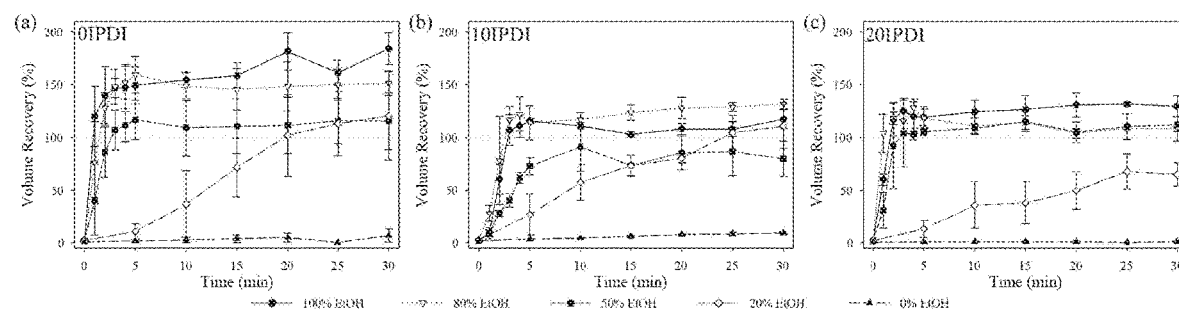
FIG. 3 depicts volume recovery in EtOH solutions. Volume recovery is shown over time submerged in EtOH solutions with varying concentrations for SMP foam compositions of (a) 0IPDI, (b) 10IPDI, and (c) 20IPDI. A dashed line is shown at 100% volume recovery to indicate where the actuated volume equals the precompressed volume.

Average volume recovery for each SMP foam composition is shown in FIG. 2 for DMSO solutions and FIG. 3 for EtOH solutions. All SMP foam compositions actuated to less than 15% volume recovery in water after 30 min, with 20IPDI actuating the least amongst compositions to less than 3% volume recovery. All SMP foam compositions exhibited greater than 100% volume recovery in 100% and 90% DMSO solutions after 20 min submersion. However, DMSO concentrations less than 90% resulted in minimal actuation with only 10IPDI in 80% DMSO actuating greater than 30% volume recovery. All SMP foam compositions exhibited greater than 100% volume recovery in 100% and 80% EtOH solutions after 3 min submersion. 0IPDI and 20IPDI actuated to greater than 100% volume recovery in 50% EtOH within 3 min and all SMP foam compositions actuated greater than 50% volume recovery in 20% EtOH after 20 min.

Figure 4:
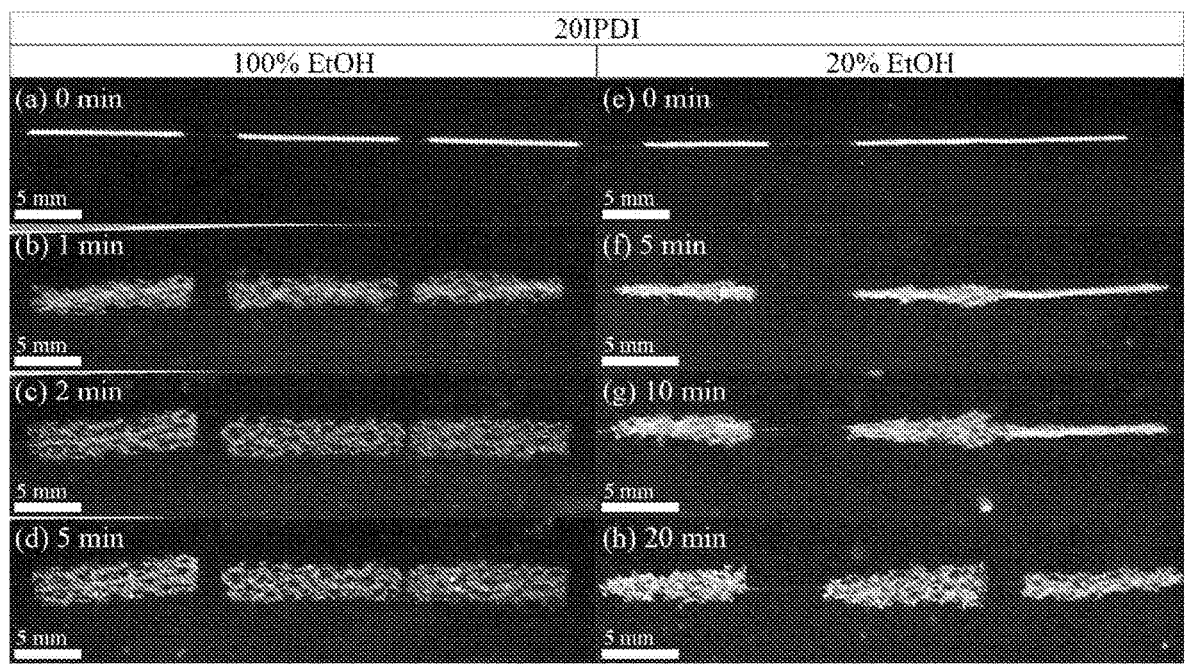
FIG. 4 includes images of 20IPDI actuation in 37° C. EtOH solutions. (a), (b), (c), and (d) show 20IPDI actuation in 100% EtOH at 0, 1, 2, and 5 min, respectively. (e), (f), (g) and (h) show 20IPDI actuation in 20% EtOH at 0, 5, 10, and 20 min, respectively.

Volume recovery testing demonstrated that submersion in water resulted in minimal foam actuation for all compositions while DMSO and EtOH both stimulated actuation with a solvent concentration dependence. FIG. 4 shows selected images of the foam actuation in 100% and 20% EtOH solutions. For the studies related to FIG. 4, all SMP foam compositions actuated to less than 15% volume recovery in water after 30 min, with 20IPDI actuating the least amongst compositions to less than 3% volume recovery. All SMP foam compositions exhibited greater than 100% volume recovery in 100% and 90% DMSO solutions after 20 min submersion. However, minimal actuation was observed in DMSO concentrations less than 90%, with only 10IPDI in 80% DMSO actuating greater than 30% volume recovery. All SMP foam compositions exhibited greater than 100% volume recovery in 100% and 80% EtOH solutions after 3 min submersion. 0IPDI and 20IPDI actuated to greater than 100% volume recovery in 50% EtOH within 3 min, and 0IPDI and 10IPDI actuated to greater than 100% volume recovery in 20% EtOH within 25 min. Volume recovery testing demonstrates a plasticization sensitivity to EtOH that is not shown with DMSO, where the EtOH is sufficiently more effective as a plasticizer over water, even in dilute concentrations.

In some embodiments both swelling and shape memory effects are critical factors in the SMP foam volume recovery shown in this study. Previous studies on solvent stimulated actuation have reported that swelling of solvent into the polymer matrix changes the internal energy and decreases the relaxation time. In embodiments foam compositions exhibited swelling to greater than their original volumes during submersion in 100% solutions of both DMSO and EtOH. The rates of volume ratio $$\left[\text{Volume Ratio \%} = \left(\frac{\text{Volume}_{Submersion\ Time\ Point}}{\text{Volume}_{Initial}}\right) \times 100\right]$$

increase during the swelling and volume recovery are very similar for all foam compositions. However, while EtOH exposure resulted in an expected decrease in relaxation time and Tg (tan δmax) values below 37° C. for all foam compositions, DMSO exposure did not cause the same result. Rather, for 20IPDI DMSO exposure resulted in polymer swelling but minimal to no relaxation in DMA kinetic experiments. This suggests differing mechanisms through which DMSO and EtOH influence volume recovery. During swelling, solvent penetrates into the polymer matrix and separates the polymer chains, increasing overall volume and enabling viscous migration between polymer network and solvent. During shape recovery, heating the polymer above transition temperature increases chain mobility, allowing entropic forces to orient polymer chains from the organized state of the temporary shape to the disorganized state of the original shape. This suggests that DMSO exposure primarily causes volume change due to solvent swelling separating polymer chains, increasing volume, but the conformational change during polymer chain orientation expected during shape recovery is less of a factor. Thus, both swelling and shape recovery influence volume recovery, but swelling may dominate the volume change that occurs without chain relaxation expected. However, EtOH exposure was observed to cause both volume change from swelling as well as relaxation during shape recovery. Thus, rapid volume recovery occurs as a result of both swelling and shape recovery as indicated by the expected chain relaxation.

The mechanism and effectiveness of solvent stimulated actuation may be heavily dependent on the relative molecular interactions of the solvent and polymer backbone. EtOH has proved to be a much more effective plasticizer of the polyurethane-based SMP foams than DMSO and water. This may be caused by two primary factors: (1) the solvent's ability to penetrate the SMP and plasticize the polymer backbone and (2) the availability of isocyanate species to plasticization and mobility. It has been demonstrated that submersion in EtOH decreased the Tg of polyurethanes as a function of time due to hydrogen bonding interactions between the solvent and the urethane linkages. However, previous studies of solvent-stimulated actuation of polyurethanes reported opposite results to this study; namely, decreased shape recovery was observed with EtOH compared to water, which was attributed to stronger hydrogen bonding interactions between urethane linkages and water relative to those with EtOH. These differing results reinforce that interactions between the chosen solvent and specific polymer chemistry may be critical to the shape recovery effect. The SMP foam chemical compositions used in these studies were designed for increased hydrophobicity and decreased water plasticization. Methyl groups in the isocyanate monomers in combination with the ring structure of IPDI hinder water penetration into the polymer backbone, reducing available isocyanate linkages for water plasticization. The presence of both polar and non-polar regions in the EtOH molecule may allow for drastically increased interactions with this polymer backbone compared to water and DMSO. Specifically, the OH functionality in the EtOH molecule will readily interact with urethane linkages while the C—C tail will interact with the non-polar regions of the isocyanates.

In an embodiment solvent-stimulated volume recovery of hydrophobic polyurethane-based SMP foams using DMSO and EtOH was shown. Dramatic decreases in $T_g$ were observed with exposure to water, DMSO, and EtOH. EtOH was shown to decrease SMP foam relaxation times to less than 1 min in DMA kinetic experiments. Furthermore, rapid shape recovery and volume swelling was observed for SMP foams in high concentrations of both DMSO and EtOH, as well as in decreased concentrations of EtOH. This demonstrates effective control of SMP foam volume recovery using both DMSO and EtOH, including in aqueous environments, and that pairing of polymer composition and solvent selection may be critical in some instances to the effectiveness of this actuation technique. Results described herein shows SMP foam actuation control using non-water solvents. This demonstrates applications for use of solvents as an alternative actuation stimulant for polyurethane-based SMP foams and may improve feasibility of using SMP materials in a variety of applications. Additional example embodiments now follow.

Example 1 includes a system comprising: a polyurethane shape memory polymer (SMP) foam that transitions from a secondary shape to a primary shape when the foam is heated above its glass transition temperature (Tg); a solvent; and a catheter including the foam compressed into its secondary shape; wherein (a) the Tg is above 38 degrees C. when the foam is dry and the solvent plasticizes the Tg to below 38 degrees C. when applied to the foam.

Example 2 includes the system of example 1, wherein the solvent includes a member selected from the group comprising: a lipid emulsion, isopropyl alcohol, acetic acid, dimethyl sulfoxide (DMSO), cumene, ethyl acetate, formic acid, lactic acid, ethyl alcohol (ethanol), and a perfluorocarbon.

Example 3 includes the system of example 1, wherein both the foam and the solvent are hydrophobic.

Example 4 includes the system of example 2, wherein the foam is open cell, aliphatic, and exhibits transverse anisotropy.

Example 5 includes the system of example 3, wherein the foam includes a backbone having regularly spaced alkene groups.

Example 6 includes the system of example 4, wherein alkene groups are crosslinked to each other to render the foam a thermoset SMP.

Example 7 includes the system of example 6, wherein the foam includes at least one diisocyanate monomer and at least one polyfunctional diol.

Example 8 includes the system of example 7, wherein the at least one diisocyanate monomer is selected from the group comprising hexamethylene diisocyanate, trimethylhexamethylene diisocyanate, and isophorone diisocyanate.

Example 9 includes the system of example 7, wherein the at least one diisocyanate monomer includes isophorone diisocyanate and an additional member selected from the group comprising hexamethylene diisocyanate and trimethylhexamethylene diisocyanate.

Example 10 includes the system of example 9, wherein the at least one polyfunctional diol is selected from the group comprising hydroxypropyl ethylenediamine and triethanolamine.

Example 11 includes the system of example 9, wherein the at least one polyfunctional diol includes a perfluoronated diol.

Example 12 includes the system of example 7, wherein the at least one polyfunctional diol includes a member selected from the group comprising: (2,2,3,3-Tetrafluoro-1,4-butanediol), (2,2,3,3,4,4-Hexafluoro-1,5-pentanediol), (2,2,3,3,4,4,5,5-Octafluoro-1,6-hexanediol), (1H,1H,8H,8H-Perfluoro-3,6-dioxaoctan-1,8-diol), (2,2,3,3,4,4,5,5,6,6,7,7-Dodecafluoro-1,8-octanediol), (1H,1H,11H,11H-Perfluoro-3,6,9-trioxaundecan-1,11-diol), (2,2,3,3,4,4,5,5,6,6,7,7,8,8-Tridecafluoro-1,9-nonanediol), (2,2,3,3,4,4,5,5,6,6, 7,7,8,8,9,9-Hexadecafluoro-1,10-decanediol), (2,2,3,3,4,4, 5,5,6,6,7,7,8,8,9,9,10,10,11,11-Eiacosafluoro-1,12-dodecanediol).

An embodiment includes one or more of the following 3 solvents: (1) ethanol, (2) DMSO, (3) perfluorocarbons class of solvents. Embodiments provide advantages by coupling a foam to a given solvent. For solvent (1), foams may include TMHDI with some IPDI. IPDI is even more hydrophobic than TMHDI and ensures no actuation in water, but ethanol will still plasticize the material below body temp. Solvents (1) and (2) may be most suitable for applications outside of the brain (e.g., peripheral vessels). Solvent (3) may be used with foams described in, for example, the patent entitled "Post Polymerization Cure Shape Memory Polymers", U.S. Pat. No. 8,883,871, granted Nov. 11, 2014. Example 12 may substitute a portion of the diols (OH—R2-OH) described in FIG. 1 of U.S. Pat. No. 8,883,871 with fluorinated diols such as those described immediately above for example 12. These diols may make the material more susceptible to being plasticized by perfluorocarbon solvents, and such diols are hydrophobic.

Example 13 includes the system of example 2, wherein the solvent includes the perfluorocarbon and the perfluorocarbon is selected from the group comprising perflourodecalin, perflourophenanthrene, and perflouro-n-hexane.

Example 14 includes the system of example 2, wherein the solvent includes ethyl alcohol (ethanol).

Example 15 includes the system of example 14, wherein the ethyl alcohol (ethanol) has a concentration greater than 30%.

Example 16 includes the system of example 2, wherein the solvent includes DMSO.

Example 17 includes the system of example 16, wherein the DMSO has a concentration greater than 85%.

Example 18 includes the system of example 2 comprising no heat source based on optical or resistive heating.

Example 19 includes the system of example 2 wherein: the foam does not self actuate to greater than 50% recovery of the primary shape within 30 minutes of exposure to an aqueous environment at less than 38 degrees C.; and the aqueous environment includes at least one of blood, saline, and water.

Example 20 includes the system of example 2, wherein the solvent diffuses through the foam more quickly than water diffuses through the foam.

Example 21 includes a system comprising: a polyurethane shape memory polymer (SMP) foam that transitions from a secondary shape to a primary shape when the foam is heated above its glass transition temperature (Tg); a solvent; and a catheter including the foam compressed into its secondary shape; wherein (a) the Tg is above 38 degrees C. when the foam is dry and the solvent plasticizes the Tg to below 38 degrees C. when applied to the foam.

Example 22 includes the system of example 21, wherein the solvent is selected from a group comprising an alcohol, ketone, hydrocarbon, chlorinated hydrocarbon, fluorinated hydrocarbon, perfluorocarbon, ester, ether, hydroxyether, glycol ether, glycol ester, acid solution in water, base solution in water, and saline.

Example 1a includes a shape memory polymer device that can be fixed into a secondary geometry and stimulated back to its primary geometry when stimulated, a solvent with solubility parameters that promote diffusion into the shape memory polymer device, wherein the SMP includes a dry transition temperature above body temperature and a solvent plasticized temperature below body temperature, wherein the SMP solubility parameters for water promote slower moisture diffusion than the device system solvent, wherein when the SMP, deployed within a medium in a temperature range of 35-39 C, and exposed to the solvent at temperature 37 C, the transition temperature lowers to below 37 C due to solvent plasticization Example 2a includes the device of example 1a wherein said activating solvent is an alcohol, ketone, perfluorocarbon, ester, ether, hydroxyether, glycol ether, glycol ester, acid solution in water, base solution in water, or saline.

Example 3a includes a device featuring a shape memory polymer foam not activated with exposure to a non-activating solvent at or near surrounding media temperature and activated with exposure of the shape memory polymer foam to an activating solvent at or near surrounding media temperature, comprising: a. a shape memory polymer where shape memory polymer is defined as a polymer material capable of maintaining a programmed secondary geometry until activated to change geometry to a primary shape, b. a shape memory polymer foam with an open cell foam structure, c. a shape memory polymer foam with a shape memory effect about a characteristic transition temperature activated with exposure of the shape memory polymer foam to an activating solvent, d. a shape memory polymer foam with shape memory effect about a characteristic transition temperature not activated with exposure of the shape memory polymer foam to a non-activating solvent, e. surrounding media temperature defined as the temperature of the media in proximity to or in contact with or surrounding the device.

Example 4a includes the device of example 3a wherein said activating solvent is an alcohol, ketone, perfluorocarbon, ester, ether, hydroxyether, glycol ether, glycol ester, acid solution in water, base solution in water, or saline.

Example 1b includes a device featuring a shape memory polymer foam activated with exposure of the shape memory polymer foam to an activating solvent at or near surrounding media temperature, comprising: a. a shape memory polymer where shape memory polymer is defined as a polymer material capable of maintaining a programmed secondary geometry until activated to change geometry to a primary shape, b. a shape memory polymer foam with an open cell foam structure, c. a shape memory polymer foam with a shape memory effect about a characteristic transition temperature activated with exposure of the shape memory polymer foam to an activating solvent, d. surrounding media temperature defined as the temperature of the media in proximity to or in contact with or surrounding the device.

Example 2b includes the device of example 1b wherein said activating solvent is an alcohol.

Example 3b includes the device of example 1b wherein said activating solvent is a ketone.

Example 4b includes the device of example 1b wherein said activating solvent is a hydrocarbon.

Example 5b includes the device of example 1b wherein said activating solvent is a chlorinated hydrocarbon.

Example 6b includes the device of example 1b wherein said activating solvent is a fluorinated hydrocarbon.

Example 7b includes the device of example 1b wherein said activating solvent is an ester.

Example 8b includes the device of example 1b wherein said activating solvent is an ether.

Example 9b includes the device of example 1b wherein said activating solvent is a hydroxyether.

Example 10b includes the device of example 1b wherein said activating solvent is a glycol ether.

Example 11b includes the device of example 1b wherein said activating solvent is a glycol ester.

Example 12b includes the device of example 1b wherein said activating solvent is water.

Example 13b includes the device of example 1b wherein said activating solvent is an acid solution in water.

Example 14b includes the device of example 1b wherein said activating solvent is a base solution in water.

Example 15b includes the device of example 1b wherein said activating solvent is saline.

Example 16b includes the device of example 1b wherein said activating solvent is blood.

Example 17b includes a device featuring a shape memory polymer foam not activated with exposure of the shape memory polymer foam to a non-activating solvent at or near surrounding media temperature and activated with exposure of the shape memory polymer foam to an activating solvent at or near surrounding media temperature, comprising: a. a shape memory polymer where shape memory polymer is defined as a polymer material capable of maintaining a programmed secondary geometry until activated to change geometry to a primary shape, b. a shape memory polymer foam with an open cell foam structure, c. a shape memory polymer foam with a shape memory effect about a characteristic transition temperature activated with exposure of the shape memory polymer foam to an activating solvent, d. a shape memory polymer foam with shape memory effect about a characteristic transition temperature not activated with exposure of the shape memory polymer foam to a non-activating solvent, e. surrounding media temperature defined as the temperature of the media in proximity to or in contact with or surrounding the device.

Example 18b includes the device of example 17b wherein said activating solvent is an alcohol.

Example 19b includes the device of example 17b wherein said activating solvent is a ketone.

Example 20b includes the device of example 17b wherein said activating solvent is a hydrocarbon.

Example 21b includes the device of example 17b wherein said activating solvent is a chlorinated hydrocarbon.

Example 22b includes the device of example 17b wherein said activating solvent is a fluorinated hydrocarbon.

Example 23b includes the device of example 17b wherein said activating solvent is an ester.

Example 24b includes the device of example 17b wherein said activating solvent is an ether.

Example 25b includes the device of example 17b wherein said activating solvent is a hydroxyether.

Example 26b includes the device of example 17b wherein said activating solvent is a glycol ether.

Example 27b includes the device of example 17b wherein said activating solvent is a glycol ester.

Example 28b includes the device of example 17b wherein said activating solvent is water.

Example 29b includes the device of example 17b wherein said activating solvent is an acid solution in water.

Example 30b includes the device of example 17b wherein said activating solvent is a base solution in water.

Example 31b includes the device of example 17b wherein said activating solvent is saline.

Example 32b includes the device of example 17b wherein said activating solvent is blood.

Example 33b includes the device of example 17b wherein said non-activating solvent is an alcohol.

Example 34b includes the device of example 17b wherein said non-activating solvent is a ketone.

Example 35b includes the device of example 17b wherein said non-activating solvent is a hydrocarbon.

Example 36b includes the device of example 17b wherein said non-activating solvent is a chlorinated hydrocarbon.

Example 37b includes the device of example 17b wherein said non-activating solvent is a fluorinated hydrocarbon.

Example 38b includes the device of example 17b wherein said non-activating solvent is an ester.

Example 39b includes the device of example 17b wherein said non-activating solvent is an ether.

Example 40b includes the device of example 17b wherein said non-activating solvent is a hydroxyether.

Example 41b includes the device of example 17b wherein said non-activating solvent is a glycol ether.

Example 42b includes the device of example 17b wherein said non-activating solvent is a glycol ester.

Example 43b includes the device of example 17b wherein said non-activating solvent is water.

Example 44b includes the device of example 17b wherein said non-activating solvent is an acid solution in water.

Example 45b includes the device of example 17b wherein said non-activating solvent is a base solution in water.

Example 45b includes the device of example 17b wherein said non-activating solvent is saline.

Example 46b includes the device of example 17b wherein said non-activating solvent is blood.

The foregoing description of the embodiments of the invention has been presented for the purposes of illustration and description. It is not intended to be exhaustive or to limit the invention to the precise forms disclosed. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A system comprising:
   a polyurethane shape memory polymer (SMP) foam that transitions from a secondary shape to a primary shape when the foam is heated above its glass transition temperature (Tg);
   a solvent that includes a perfluorocarbon; and
   a catheter including the foam compressed into its secondary shape;
   wherein the Tg is above 38 degrees C. when the foam is dry;
   wherein the solvent is configured to plasticize the SMP foam so the Tg itself drops below 38 degrees C. when the solvent is applied to the foam; and
   wherein the foam includes at least one polyfunctional diol, the at least one polyfunctional diol including at least one perfluoronated diol.

2. The system of claim 1, wherein both the foam and the solvent are hydrophobic.

3. The system of claim 2, wherein the foam is open cell, aliphatic, and exhibits transverse anisotropy.

4. The system of claim 2, wherein the foam includes a backbone having regularly spaced alkene groups.

5. The system of claim 3, wherein the alkene groups are crosslinked to each other to render the foam a thermoset SMP.

6. The system of claim 1, wherein the foam includes at least one diisocyanate monomer.

7. The system of claim 6, wherein the at least one diisocyanate monomer includes isophorone diisocyanate.

8. The system of claim 6, wherein the at least one diisocyanate monomer includes isophorone diisocyanate and at least one of hexamethylene diisocyanate, trimethyl-hexamethylene diisocyanate, or combinations thereof.

9. The system of claim 8, wherein the foam includes at least one of hydroxypropyl ethylenediamine, triethanolamine, or combinations thereof.

10. The system of claim 1, wherein the at least one perfluoronated diol includes at least one of: (2,2,3,3-Tetrafluoro-1,4-butanediol), (2,2,3,3,4,4-Hexafluoro-1,5-pentanediol), (2,2,3,3,4,4,5,5-Octafluoro-1,6-hexanediol), (1H,1H,8H,8H-Perfluoro-3,6-dioxaoctan-1,8-diol), (2,2,3,3,4,4,5,5,6,6,7,7-Dodecafluoro-1,8-octanediol), (1H,1H,11H,11H-Perfluoro-3,6,9-trioxaundecan-1,11-diol), (2,2,3,3,4,4,5,5,6,6,7,7,8,8-Tridecafluoro-1,9-nonanediol), (2,2,3,3,4,4,5,5,6,6,7,7,8,8,9,9-Hexadecafluoro-1,10-decanediol), (2,2,3,3,4,4,5,5,6,6,7,7,8,8,9,9,10,10,11,11-Eiacosafluoro-1,12-dodecanediol), or combinations thereof.

11. The system of claim 1, wherein the perflourocarbon includes at least one of perflourodecalin, perflourophenanthrene, perflouro-n-hexane, or combinations thereof.

12. The system of claim 1, wherein the solvent includes ethyl alcohol (ethanol).

13. The system of claim 12, wherein the ethyl alcohol (ethanol) has a concentration greater than 30%.

14. The system of claim 1, wherein the solvent includes DMSO.

15. The system of claim 14, wherein the DMSO has a concentration greater than 85%.

16. The system of claim 1 comprising no heat source based on optical or resistive heating.

17. The system of claim 1 wherein:
the foam is configured to not self actuate to greater than 50% recovery of the primary shape within 30 minutes of exposure to an aqueous environment at less than 38 degrees C.; and
the aqueous environment includes at least one of blood, saline, water, or combinations thereof.

18. The system of claim 1, wherein the solvent diffuses through the foam more quickly than water diffuses through the foam.

19. The system of claim 1, wherein the SMP foam is a thermoset polymer.

20. The system of claim 6, wherein the SMP foam is a thermoset polymer.

* * * * *